United States Patent
Meffert et al.

(10) Patent No.: US 6,399,679 B1
(45) Date of Patent: Jun. 4, 2002

(54) THICKENERS FOR SURFACTANT-CONTAINING COMPOSITIONS

(75) Inventors: Helmut Meffert, Mannheim; Kristin Tiefensee, Westheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/371,847

(22) Filed: Aug. 11, 1999

(30) Foreign Application Priority Data

Aug. 14, 1998 (DE) .......................................... 198 36 808

(51) Int. Cl.[7] .................................................. C08K 5/07
(52) U.S. Cl. .......................... 524/58; 524/27; 524/556; 524/560; 524/561; 526/328.5
(58) Field of Search .......................... 526/328.5; 524/27, 524/58, 556, 560, 561

(56) References Cited

U.S. PATENT DOCUMENTS

| | | | |
|---|---|---|---|
| 3,915,921 A | 10/1975 | Schlatzer, Jr. ................. | 260/17 |
| 4,432,881 A | * 2/1984 | Evani ....................... | 252/8.5 A |

FOREIGN PATENT DOCUMENTS

| | | |
|---|---|---|
| CA | 2237058 | 6/1997 |
| EP | 268164 | 5/1988 |
| WO | 97/21744 | 6/1997 |
| WO | 98/31334 | 7/1998 |

* cited by examiner

Primary Examiner—Helen L. Pezzuto
(74) Attorney, Agent, or Firm—Keil & Weinkauf

(57) ABSTRACT

Use of neutralized or partially neutralized copolymers obtainable from

A) from 50 to 99% by weight of monoethylenically unsaturated carboxylic acid and
B) from 1 to 50% by weight of at least one comonomer chosen from the groups a) to d) or also mixtures of different monomers from groups a) to d)
  a) monoethylenically unsaturated carboxylic acid esters with a saturated $C_8$- to $C_{30}$-alcohol
  b) N-alkyl- or N,N-dialkyl-substituted carboxamides, the alkyl radicals independently of one another being aliphatic or cycloaliphatic alkyl radicals having at least 8 to 18 carbon atoms,
  c) vinyl esters of aliphatic $C_8$- to $C_{30}$-carboxylic acids,
  d) $C_8$- to $C_{18}$-alkyl vinyl ethers, for the preparation of hair cleansers.

18 Claims, No Drawings

THICKENERS FOR SURFACTANT-CONTAINING COMPOSITIONS

The present invention relates to the use of hydrophobically modified polymers of monoethylenically unsaturated carboxylic acids as thickeners in hair cleansers, and to aqueous compositions which comprise these polymers.

Thickeners are used widely to increase the viscosity of aqueous preparations, for example in the field of pharmaceuticals and cosmetics. Examples of frequently used thickeners are fatty acid polyethylene glycol monoesters, fatty acid polyethylene glycol diesters, fatty acid alkanolamides, ethoxylated fatty alcohols, ethoxylated glycerol fatty acid esters, cellulose ethers, sodium alginate, polyacrylic acids and neutral salts.

The use of known thickeners is, however, depending on the preparation to be thickened, associated with disadvantages. For example, the thickening action and the salt stability of the thickener can be unsatisfactory, and their incorporation into the preparation to be thickened can be hindered.

U.S. Pat. No. 3,915,921 (The B.F. Goodrich Company) describes copolymers comprising 95–50% by weight of monoethylenically unsaturated carboxylic acids and 5–50% by weight of an acrylic acid or methacrylic acid ester of a $C_{10}$–$C_{30}$ fatty alcohol. Optionally, the polymers can be crosslinked. The copolymers are used as thickeners for toothpastes and printing pastes.

EP 0 268 164 (The B.F. Goodrich Company) describes the use of crosslinked copolymers of monoolefinically unsaturated acids (50–99% by weight) and alkyl esters of monoolefinically unsaturated acids (50–1% by weight) (crosslinked with pentaerythritol triallyl ether), which are known under the CTFA name "Acrylates/$C_{10-30}$-Alkyl Acrylate Crosspolymer". The latter are used to stabilize O/W emulsions in cosmetic and pharmaceutical preparations such as, for example, skin creams, skin lotions and gels.

In WO 97/21744 (BASF Aktiengesellschaft) copolymers which have to be crosslinked are used.

These polymers are precipitation polymers and are free-flowing powders which are stirred into water and then neutralized. This neutralization step is necessary in order to convert the acidic polymers into the carboxylates, which are ultimately responsible for the viscosity.

It is known that these crosslinked (hyhdrophobically modified) polyacrylic acids in the neutralized state react very sensitively to salt. The viscosity breaks up. For this reason, it is unusual to use these polymers in shampoo formulations as viscosity-imparting agents. Because of the salt concentrations present therein (surfactants, surfactant mixtures, NaCl as impurity in surfactants) it is not possible for viscosity to form. The presence of cationic auxiliaries leads to complex formation and precipitation.

EP 0128 237 (The B.F. Goodrich Company) describes weakly crosslinked copolymers (0.1 to 1.0% by weight) of monoethylenically unsaturated carboxylic acids (95.5 to 98.9% by weight) and esters of these carboxylic acids (1 to 2.5% by weight) for use as thickeners in a printing paste.

U.S. Pat. No. 4,432,881 (Dow Chemical Company) describes copolymers of water-soluble monomers such as, for example, acrylamide, acrylic acid etc., preferably the combinations thereof, and N-alkylacrylamides and acrylic esters. The hydrophilic/hydrophobic fraction ratios are from 98:2 mol % to 99.995:0.005 mol %, preferably from 99:1 mol % to 99.9:0.1 mol %. The molecular weights are between 200,000–5,000,000 g/mol, preferably between 800,000–2,5000,000 g/mol. The resulting polymers are used as dispersible hydrophobic thickeners, used in formulations comprising the described polymers, a nonionic surface-active substance (HLB 2–15) and an inorganic salt for increasing the viscosity of water.

U.S. Pat. No. 4,395,524 (Rohm and Haas Company) describes the copolymerization of hydrophilic components (e.g. acrylamide, acrylic acid, N-vinylpyrrolidone etc.) with N-alkylacrylamides (alkyl=$C_{10}$ to $C_{36}$, preferably $C_{12}$ to $C_{22}$). The copolymerization is carried out as precipitation polymerization or polymerization in solution. The molecular weight of the polymers described is $M_w$>30,000 g/mol. The resulting polymers are used as thickeners of aqueous systems, sedimentation stabilizers, surface-active substances or disperrants.

WO 98/31334 describes hair conditioners which do not comprise salts, are not clear and comprise water-insoluble components such as silicone oil and fatty alcohols as active component.

It is an object of the present invention to provide a thickener which can be stirred into a formulation without problem. The formulation preferably comprises at least one alkyl or alkenyl polyglycoside. Such formulations are used inter alia in the cosmetics industry, in particular in hair cleansers, in particular in shampoos. The resulting formulation should be clear and stable and thicken as a result of the addition of the polymers according to the invention.

Surprisingly, we have now found that neutralized, hydrophobically modified polymers of monoethylenically unsaturated carboxylic acids are highly suitable as thickeners for surfactant-containing compositions, e.g. in mild shampoo formulations, in particular for compositions which comprise an alkyl or alkenyl polyglycoside. The formulations according to the invention are clear. The abovementioned disadvantages are not observed here.

We have found that this object is achieved by copolymers which comprise at least 50% by weight and at most 99% by weight of monoethylenically unsaturated carboxylic acid. Preference is given to polymers containing at least 58% by weight and at most 99% by weight of monoethylenically unsaturated carboxylic acid, and very particular preference is given to polymers with a content of monoethylenically unsaturated carboxylic acid of from 65% by weight to 99% by weight.

The polymers are prepared by free-radical polymerization of the corresponding monomers, which in each case comprise at least 50% by weight of monoethylenically unsaturated carboxylic acid.

The hydrophobic component used is at least 1, at most 50% by weight of an a) monoethylenically unsaturated carboxylic acid ester with a saturated $C_8$- to $C_{30}$-alcohol, preferably a $C_8$- to $C_{18}$-alcohol (e.g. octyl acrylate, 2-ethylhexyl acrylate, nonyl acrylate, decyl acrylate, lauryl acrylate, myristyl acrylate, cetyl acrylate, stearyl acrylate, behenyl acrylate, hexyl methacrylate, octyl methacrylate, nonyl methacrylate, decyl methacrylate, lauryl methacrylate, myristyl methacrylate, cetyl methacrylate, stearyl methacrylate, behenyl methacrylate, tert-butylcyclohexyl acrylate). In this connection, particular importance is attached to the acrylic or methacrylic esters of fatty alcohols having from 8 to 18 carbon atoms.

As an alternative to the monoethylenically unsaturated carboxylic acid esters, it is possible to also use b) N-alkyl- or N,N-dialkyl-substituted carboxamides, the alkyl radicals independently of one another being aliphatic or cycloaliphatic alkyl radicals having at least 8 carbon atoms (e.g. N-stearylacrylamide, N-stearylmethacrylamide, N-(1-mehtyl)undecyl acrylate, N-(1-mehtyl)undecyl methacrylate, N-dodecylacrylamide, N-dodecylmethacrylamide, N-octylacrylamide, N-octylmethacrylamide, N,N-dioctylacrylamide, N,N-dioctylmethacrylamide, N-cetylacrylamide, N-cetylmethacrylamide, N-dodecylacrylamide, N-dodecylmethacrylamide, N-myristylacrylamide, N-myristylmethacrylamide, N-(2-ethyl)hexylacrylamide, N-(2-ethyl)hexylmethacrylamide Particular preference is given to $C_8$ to $C_{18}$-alkyl radicals.

As a further alternative to the monoethylenically unsaturated carboxylic acid esters, it is also possible to use c) vinyl esters of long-chain aliphatic carboxylic acids ($C_8$ to $C_{30}$ carboxylic acids). Preference is given to using vinyl esters of $C_8$ to $C_{18}$ carboxylic acids.

In addition, it is possible to use d) alkyl vinyl ethers, preferably those containing $C_8$ to $C_{18}$-alkyl radicals.

It is of course also possible to use mixtures of two or more carboxylic acid esters, carboxamides, vinyl esters or alkyl vinyl ethers, provided the sum of the contents of these comonomers does not exceed 50% by weight.

As the hydrophilic component, it is possible to use the following copolymerizable monoethylenically unsaturated carboxylic acids (or else mixtures thereof) (from 50 to 99% by weight, preferably from 58 to 99% by weight, particularly preferably from 65 to 99% by weight):

Monoethylenically unsaturated carboxylic acids having from 3 to 8 carbon atoms, such as acrylic acid, methacrylic acid, dimethacrylic acid, ethacrylic acid, maleic acid, citraconic acid, methylenemalonic acid, allylacetic acid, vinylacetic acid, crotonic acid, fumaric acid, mesaconic acid and itaconic acid, are preferred.

From this group of monomers, preference is given to using acrylic acid, methacrylic acid, maleic acid or mixtures of said carboxylic acids.

The monoethylenically unsaturated carboxylic acids can be used in the copolymerization in the form of the free acid and—provided they exist—the anhydrides, or in partially or in completely neutralized form. These monomers are preferably neutralized using alkali metal bases or alkaline earth metal bases, ammonia or amines, e.g. sodium hydroxide solution, potassium hydroxide solution, soda, potash, sodium hydrogen carbonate, magnesium oxide, calcium hydroxide, calcium oxide, gaseous or aqueous ammonia, triethyldmine, ethanolamine, diethanolamine, triethanolamine, morpholine, diethylenetriamine or tetraethylenepentamine.

Other suitable comonomers are, for example, the $C_1$–$C_4$-esters, N—$C_1$–$C_4$-alkyl- or N,N—$C_1$–$C_4$-dialkyl-substituted amides, where the alkyl radicals of the dialkylamide can be identical or different, and nitriles of the abovementioned carboxylic acids, e.g. methyl acrylate, ethyl acrylate, methyl methacrylate, ethyl methacrylate, hydroxyethyl acrylate, hydroxypropyl acrylate, hydroxybutyl acrylate, hydroxyethyl methacrylate, hydroxypropyl methacrylate, hydroxyisobutyl acrylate, hydroxyisobutyl methacylate, monomethyl maleate, dimethyl maleate, monoethyl maleate, diethyl maleate, 2-ethylhexyl acrylate, 2-ethylhexyl methacrylate, acrylamide, methacrylamide, N-dimethylacrylamide, N-tert-butylacrylamide, acrylonitrile, methacrylonitrile, dimethylaminoethyl acrylate, diethylaminoethyl acrylate, diethylaminoethyl methacrylate and the salts of the last-named monomers with carboxylic acids or mineral acids and the quaternized products. Each of the alkyl groups in the esters and amides can be hydroxy-substituted.

In addition, other suitable copolymerizable monomers are acrylamidoglycolic acid, vinylsulfonic acid, allylsulfonic acid, methallylsulfonic acid, styrenesulfonic acid, 3-sulfopropyl acrylate, 3-sulfopropyl methacrylate and acrylamidomethylpropane-sulfonic acid, and monomers containing phosphonic acid groups, such as vinylphosphonic acid, allylphosphonic acid and acrylamidomethanepropanephosphonic acid.

Other suitable copolymerizable compounds are N-vinylpyrrolidone, N-vinylcaprolactam, N-vinylimidazole, N-vinyl-2-methylimidazole, N-vinyl-4-methylimidazole, diallylammonium chloride, vinyl acetate and vinylpropionate. It is of course also possible to use mixtures of said monomers.

The monoethylenically unsaturated carboxylic acid and the hydrophobic component or components and, where present, the other suitable monomers total 100%.

The copolymers are prepared by known processes, for example solution, precipitation or inverse suspension polymerization using compounds which form free radicals under the polymerization conditions.

The polymerization temperatures are usually in the range from 30° C. to 200° C., preferably from 40° C. to 140° C. Examples of suitable initiators are azo and peroxy compounds, and the customary redox initiator systems, such as combinations of hydrogen peroxide and reductive compounds, e.g. sodium sulfite, sodium bisulfite, sodium formaldehyde sulfoxylate and hydrazine.

The copolymers have K values of at least 10 and are essentially uncrosslinked. They preferably have a K value of from 12 to 70, particularly preferably from 15 to 50. The K values are determined in accordance with H. Fikentscher, Cellulose-Chemie, Volume 13, 58 to 64 and 71 to 74 (1932) in a 0.1 molar aqueous NaCl solution at 25° C., at concentrations between 0.1% and 5% depending on the K value range.

The present invention also relates to aqueous compositions which comprise at least one neutralized or partially neutralized, hydrophobically modified polymeric carboxylic acid of the nature described above, and at least one surfactant.

The invention further relates to aqueous compositions which comprise
 a) at least one alkyl or alkenyl polyglycoside, in particular a $C_8$–$C_{18}$-alkyl or $C_8$–$C_{18}$-alkenyl polyglycoside,
 b) at least one hydrophobically modified polymeric carboxylic acid having the composition described above,
 c) optionally another surfactant different from a), and
 d) a neutral salt and
 e) other auxiliaries such as preservatives, emulsifiers, perfume oils, care substances such as panthenol, collagen, vitamins, protein hydrolysates, stabilizers, pH regulators, dyes, pearlizing agents, bodying agents, silicones, humectants, refatting agents, salts, acids (for example lactic acid, citric acid) and other customary additives.

The polyglycosides are preferably polyglucosides, which are a homolog mixture obtained by acetylation of glucose with fatty alcohols. The average number of glucose units per molecule is in the range from 1 to 3.

A preferred alkylpolyglucoside (APG) is Plantaren®, in which from 1 to 7 glucose units are linked glycosidally to a fatty alcohol (usually 12 carbon atoms). Preferably, 2 glucose units are linked.

The content of polyglucosides is preferably at most 60% by weight.

The abovedescribed polymers are generally present in the compositions in an amount of at least 0.2% by weight, preferably up to 30% by weight, particularly preferably in an amount of at least 0.5 to 20% by weight, based on the total weight of the composition.

The surfactant present in the compositions according to the invention may be anionic, nonionic, cationic or amphoteric.

Suitable anionic surfactants are, for example, alkyl sulfates, alkyl ether sulfates, alkylarylsulfonates, alkyl succinates, alkyl sulfosuccinates, N-alkoyl sarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably from 1 to 3 ethylene oxide units, in the molecule.

Suitable examples are sodium lauryl sulfate, ammonium lauryl sulfate, sodium lauryl ether sulfate, ammonium lauryl ether sulfate, sodium lauryl sarcosinate, sodium oleyl succinate, ammonium lauryl sulfosuccinate, sodium dodecylbenzenesulfonate, triethanolamine dodecylbenzenesulfonate.

Suitable amphoteric surfactants are, for example, alkylbetaines, alkylamidopropylbetaines, alkylsulfobetaines, alkyl glycinates, alkyl carboxyglycinates, alkylamphoacetates or -propionates, alkyl amphodiacetates or -dipropionates.

For example, cocamidopropylbetaine or sodium cocamphopropionate can be used.

Examples of suitable nonionic surfactants are the reaction products of aliphatic alcohols or alkylphenols having from 6 to 20 carbon atoms in the alkyl chain, which can be linear or branched, with ethylene oxide and/or propylene oxide. The amount of alkylene oxide is from about 6 to 60 mols per mol of alcohol.

Also suitable are alkylamine oxides, mono- or dialkyl-alkanolarides, fatty acid esters of polyethylene glycols, ethoxylated fatty acid amides, alkylpolyglycosides or sorbitan ether esters.

In addition, the formulations (e.g. shampoo formulations) can comprise customary cationic surfactants, such as, for example, quaternary ammonium compounds, for example cetyltrimethylammonium chloride.

In addition, other customary cationic polymers can also be used, such as, for example, copolymers of acrylamide and dimethyldiallylammonium chloride (polyquaternium-7), cationic cellulose derivatives (polyquaternium-10), guar hydroxypropyl-trimethylammonium chloride (INCI: Hydroxypropyl Guar Hydroxy-propyltrimonium Chloride), copolymers of N-vinylpyrrolidone and quaternized N-vinylimidazole (polyquaternium-16, -44, -46) and others.

For additional thickening, the compositions according to the invention can comprise a neutral salt, in particular sodium sulfate and, preferably, sodium chloride. The neutral salt is generally present in an amount of from 0.1 to 10% by weight, in particular from 0.5 to 5% by weight.

Other additional thickeners which can be used in the formulations are, for example, PEG-55, propylene glycol oleate, PEG-120 methyl glucose dioleate and others.

In addition, the compositions according to the invention can comprise customary auxiliaries and additives known to the person skilled in the art, for example preservatives, emulsifiers, perfume oils, care substances such as panthenol, collagen, vitamins, protein hydrolysates, stabilizers, pH regulators, dyes, pearlizing agents, bodying agents, silicones, humectants, refatting agents, salts, acids (for example lactic acid, citric acid) and other customary additives.

The polymers according to the invention can also be mixed with traditional polymers customary in cosmetics in cases where very specific properties are to be set.

Other suitable cosmetics polymers (e.g. in shampoo formulations) are, for example, cationic polymers having the name poly-quaternium according to INCI, e.g. copolymers of vinyl-pyrrolidone/N-vinylimidazoliumn salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ11), copolymers of N-vinyl-caprolactam/N-vinylpyrrolidone/N-vinylimidazolium salts (Luviquat® Hold); cationic cellulose derivatives (polyquaternium-4 and -10), acrylamide copolymers (polyquaternium-7), cationic guar gum derivatives.

Other sutiable cosmetics polymers (e.g. in hair cosmetics) are also neutral polymers, such as polyvinylpyrrolidones, copolymers of N-vinylpyrrolidone and vinyl acetate and/or vinyl propionate, polysiloxanes, polyvinylcaprolactam and copolymers with N-vinylpyrrolidone, polyethylenimines and salts thereof, polyvinylamines and salts thereof, cellulose derivatives, polyasparatic acid salts and derivatives.

To set specific properties, the preparations can also comprise conditioning substances based on silicone compounds. Suitable silicone compounds are, for example, polyalkylsiloxanes, polyarylsiloxanes, polyarylalkylsiloxanes, polyether siloxanes or silicone resins.

In each case based on the total weight, the aqueous compositions according to the invention generally comprise:

from 0.2 to 20% by weight, preferably from 0.5 to 15% by weight, of at least one polymer having the composition described above, from 0 to 50% by weight of at least one surfactant and from 0.5 to 50% by weight of at least one alkyl or alkylene polyglycoside, based on the total weight of the aqueous formulation.

According to a preferred embodiment, the aqueous compositions according to the invention comprise:

a) from 0.2 to 20% by weight, preferably from 0.5 to 15% by weight, of at least one polymer having the composition described above;

b) from 1 to 50% by weight of at least one anionic surfactant, in particular an alkyl ether sulfate;

c) from 0.5 to 50% by weight of at least one $C_8$–$C_{18}$-alkyl or $C_8$–$C_{18}$-alkenyl polyglycoside;

d) from 0 to 5% by weight, preferably from 0.5 to 3% by weight, of at least one neutral salt, based on the total weight of the aqueous formulation.

These compositions according to the invention are prepared in the customary manner, it being possible to use the polymers described as such or as aqueous solutions. It is typical to stir in the thickening agent into the aqueous surfactant mixture. Auxiliaries can be stirred into the thickened mixture without problems.

The compositions according to the invention are, in particular, cosmetic or pharmaceutical copositions. Preferred cosmetic compositions are haircare compositions, in particular shampoos. The polymers described can, however, also be used in industrial preparations, such as hydraulic fluids, cleaning preparations, crop-treatment compositions, printing inks, coating compositions and preparations for animal nutrition.

The examples below illustrate the invention without limiting it.

EXAMPLES

The following thickeners were used according to the invention:

| Polymer | K value *) | Acrylic acid/stearyl methacrylate (% by weight) |
|---|---|---|
| 1 | 28 | 70/30 |
| 2 | 15 | 70/30 |
| 3 | 25 | 78/22 |
| 4 | 30 | 65/35 |

*) The K values were determined in accordance with H. Fikentscher, Cellulose-Chemie, Volume 13, 58 to 64 and 71 to 74 (1932) in a 0.1 molar aqueous NaCl solution at 25° C. using a 1% strength polymer solution The surfactant mixtures below were formulated using various polymers as thickeners; the specific compositions are summarized in Table 1:

| Formulation 1 | |
|---|---|
| Decyl glucoside | 8% |
| Sodium laureth sulfate | 4% |
| Thickener | q.s. |
| NaCl | q.s. |
| Citric acid | q.s. |
| Water | ad 100% |
| Formulation 2 | |
| Sodium/Mg laureth sulfate | |
| Sodium/Mg oleth sulfate | 10% |
| Lauryl glucoside | 4% |
| Cocoamidopropylbetain | 3% |
| Polyquaternium-16 | 2% |
| Thickener | q.s. |
| Citric acid | q.s. |
| Water | ad 100% |
| Formulation 3 | |
| Lauryl glucoside | 13% |
| Cocoamidopropylbetain | 5% |
| Cocotrimonium methosulfate | 2% |
| Hydrolyzed wheat gluten | 2% |
| Thickener | q.s. |
| Citric acid | q.s. |
| Preservative | 0.1% |
| Water | ad 100% |

TABLE 1 according to the invention

| Formulation | Polymer | Polymer content [%] | NaCl conc. [%] | Viscosity [mPas][1] | Appearance | pH |
|---|---|---|---|---|---|---|
| 1 | 1 | 3 | 3 | 3 500 | clear | 6.1 |
|   |   | 5 | 3 | 12 000 | clear | 6.1 |
|   |   | 5 | 1 | 7 900 | clear | 6.2 |
|   |   | 5 | 0 | 1 000 | clear | 6.6 |
|   | 2 | 3 | 3 | 1 200 | clear | 5.9 |
|   |   | 5 | 3 | 7 000 | clear | 6.0 |
|   | 3 | 3 | 3 | 3 700 | clear | 5.8 |
|   |   | 5 | 3 | 10 800[2] | clear | 6.1 |
| 2 | 1 | 3 | 0 | 40 000[3] | clear | 6.5 |
|   |   | 1 | 0 | 12 700 | clear | 6.5 |
| 3 | 1 | 0.5 | — | 10 100[2] | clear |   |

[1] Brookfield, 10 rpm, 23° C., spindle 3
[2] Brookfield, 10 rpm, 23° C., spindle 4
[3] Brookfield, 10 rpm, 23° C., spindle 6

TABLE 2

Comparative Examples

| Formulation | Polymer | Polymer content [%] | NaCl conc. [%] | Viscosity [mPas][1] | Appearance | pH |
|---|---|---|---|---|---|---|
| 1 | Pemulen TR 1*) | 3 | 3 | 40 600[1] | White, solid, slimy | 5.9 |
|   | Pemulen TR 1*) | 1 | — | 15 000[2] | white, slimy | 5.8 |
| 2 | Pemulen TR 1 | 3 | — | 52 000[3] | white, solid, slimy | 6.1 |

*) Products from B. F. Goodrich
[1] Brookfield, 10 rpm, 23° C., spindle 6
[2] Brookfield, 10 rpm, 23° C., spindle 4
[3] Brookfield, 10 rpm, 23° C., spindle 7

We claim:

1. A process for increasing the viscosity of an aqueous surtactant-containing composition, which comprises adding a thickening amount of at least one polymer to the composition, wherein the polymer is a neutralized or partially neutralized copolymer obtainable from
    A) from 50 to 99% by weight of monoethylenically unsaturated carboxylic acid and
    B) from 1 to 50% by weight of at least one comonomer chosen from the groups a) to d) or also mixtures of different monomers from groups a) to d)
        a) monoethylenically unsaturated carboxylic acid esters with a saturated $C_8$–$C_{30}$-alcohol,
        b) N-alkyl- or N,N-dialkyl-substituted carboxamides, the alkyl radicals independently of one another being aliphatic or cycloaliphatic alkyl radicals having at least 8 to 18 carbon atoms,
        c) vinyl esters of aliphatic $C_8$–$C_{30}$-carboxylic acids,
        d) $C_8$–$C_{18}$-alkyl vinyl ethers,
wherein the composition comprises as a surfactant at least one alkyl polyglycoside or alkenyl polyglycoside.

2. The process defined in claim 1, wherein component A is a $C_3$–$C_8$-monoethylenically unsaturated carboxylic acid and is present in an amount of from 65 to 99% by weight.

3. The process defined in claim 1, wherein the copolymer further comprises
    C) more than 0 to at most 49% by weight of at least one comonomer chosen from groups e) to h) or a mixture of monomers selected from groups e) to h)
        e) $C_1$–$C_4$-alkyl ester of a monoethylenically unsaturated carboxylic acid C,
        f) N—$C_1$–$C_4$-alkyl- or N,N—$C_1$–$C_4$-dialkyl-substituted carboxamide of a monoethylenically unsaturated carboxylic acid C, it being possible for the alkyl radicals of the dialkylamide to be identical or different,
        g) nitrile of a monoethylenically unsaturated carboxylic acid C,
        h) acrylamidoglycolic acid, vinylsulfonic acid, allylsulfonic acid, methallylsulfonic acid, styrenesulfonic acid, 3-sulfopropyl acrylate, 3-sulfopropyl methacrylate, acrylamidomethylpropanesulfonic acid, vinylphosphonic acid, allylphosphonic acid, acrylamidomethanepropanephosphonic acid, N-vinylpyrrolidone, N-vinylcaprolactam, N-vinylimidazole, N-vinyl-2-methylimidazole, N-vinyl-4-methylimidazole, diallylammonium chloride, vinyl acetate and vinyl propinate,
where the alkyl groups can be substituted with hydroxyl groups, and the monoethylenically unsaturated carboxylic acid C is selected independently of one another for groups e), f), g) from: acrylic acid, methacrylic acid, dimethacrylic acid, ethacrylic acid, maleic acid, citraconic acid, methylenemalonic acid, allylacetic acid, vinylacetic acid, crotonic acid, fumaric acid, mesaconic acid and itaconic acid.

4. The process defined in claim 1, wherein the aqueous surfactant-containing composition is a cosmetic product.

5. The process defined in claim 4, wherein the cosmetic product is a hair cleanser.

6. The process defined in claim 1, wherein the aqueous, surfactant-containing composition comprises at least one neutral salt, and
optionally at least one surfactant which is different from alkyl polyglycosides and alkenyl polyglycosides.

7. The process defined in claim 6, wherein the neutralized or partially neutralized copolymer is added to the aqueous, surfactant-containing composition in an amount of from 0.2 to 30% by weight, based on the total weight of the thickened composition.

8. The process defined in claim 6, which is adapted for the preparation of a thickened aqueous composition comprising
   a) from 0.5 to 60% by weight of the at least one surtactant selected from the group of alkyl polyglycosides and alkenyl polyglycosides,
   b) from 0.2 to 30% by weight of the neutralized or partially neutralized copolymer(s),
   c) from 1 to 50% by weight of an anionic surfactant, and
   d) from 0.1 to 5% by weight of the neutral salt(s),
based on the total weight of the thickened composition.

9. The process defined in claim 6, which is adapted for the preparation of a thickened aqueous composition comprising
   a) from 0.5 to 50% by weight of the at least one surfactant selected from the group of alkyl polyglycosides and alkenyl polyglycosides, and
   b) from 0.2 to 20% by weight of the neutralized or partially neutralized copolymer(s),
based on the total weight of the thickened composition.

10. The process defined in claim 6, which is adapted for the preparation of a thickened aqueous composition comprising
    a) from 0.5 to 50% by weight of at least one surfactant selected from the group of $C_8$–$C_{18}$-alkyl polyglycosides and $C_8$–$C_{18}$-alkenyl polyglycosides, and,
    b) from 0.5 to 15% by weight of the neutralized or partially neutralized copolymer(s),
based on the total weight of the thickened composition.

11. A thickened aqueous composition comprising
    at least one surfactant selected from the group consisting of alkyl polyglycosides and alkenyl polyglycosides,
    optionally at least one surfactant which is different from alkyl polyglycosides and alkenyl polyglycosides,
    at least one neutral salt, and
    a thickening amount of at least one neutralized or partially neutralized copolymer obtainable from
       A) from 50 to 99% by weight of monoethylenically unsaturated carboxylic acid, and
       B) from 1 to 50% by weight of at least one comonomer selected from groups a) to d) and from mixtures of different monomers from groups a) to d)
          a) monoethylenically unsaturated carboxylic acid esters with a saturated $C_8$–$C_{30}$-alcohol,
          b) N-alkyl- or N,N-dialkyl-substituted carboxamides, the alkyl radicals independently of one another being aliphatic or cycloaliphatic alkyl radicals having at least 8 to 18 carbon atoms,
          c) vinyl esters of aliphatic $C_8$–$C_{30}$-carboxylic acids,
          d) $C_8$–$C_{18}$-alkyl vinyl ethers.

12. The thickened aqueous composition defined in claim 11, wherein the neutralized or partially neutralized copolymer is present in an amount of from 0.2 to 30% by weight, based on the total weight of the thickened composition.

13. The thickened aqueous composition defined in claim 11, comprising:
    a) from 0.5 to 60% by weight of the at least one surfactant selected from the group of alkyl polyglycosides and alkenyl polyglycosides,
    b) from 0.2 to 30% by weight of the neutralized or partially neutralized copolymer(s),
    c) from 1 to 50% by weight of an anionic surfactant, and
    d) from 0.1 to 5% by weight of the neutral salt(s),
based on the total weight of the thickened composition.

14. The thickened aqueous composition defined in claim 13, comprising:
    a) from 0.5 to 50% by weight of the at least one surfactant selected from the group of alkyl polyglycosides and alkenyl polyglycosides, and
    b) from 0.2 to 20% by weight of the neutralized or partially neutralized copolymers),
based on the total weight of the thickened composition.

15. The thickened aqueous composition defined in claim 13, comprising:
    a) from 0.5 to 50% by weight of at least one surfactant selected from the group of $C_8$–$C_{18}$-alkyl polyglycosides and $C_8$–$C_{18}$-alkenyl polyglycosides, and
    b) from 0.5 to 15% by weight of the neutralized or partially neutralized copolymer(s),
based on the total weight of the thickened composition.

16. The thickened aqueous composition defined in claim 11, wherein the copolymer further comprises
    C) more than 0 to at most 49% by weight of at least one comonomer chosen from groups e) to h) or a mixture of monomers selected from groups e) to h)
    e) $C_1$–$C_4$-alkyl ester of a monoethylenically unsaturated carboxylic acid C,
    f) N—$C_1$–$C_4$-alkyl- or N,N—$C_1$–$C_4$-dialkyl-substituted carboxamide of a monoethylenically unsaturated carboxylic acid C, it being possible for the alkyl radicals of the dialkylamide to be identical or different,
    g) nitrile of a monoethylenically unsaturated carboxylic acid C,
    h) acrylamidoglycolic acid, vinylsulfonic acid, allylsulfonic acid, methallylsulfonic acid, styrenesulfonic acid, 3-sulfopropyl acrylate, 3-sulfopropyl methacrylate, acrylamidomethylpropanesulfonic acid, vinylphosphonic acid, allylphosphonic acid, acrylamidomethanepropanephosphonic acid, N-vinylpyrrolidone, N-vinylcaprolactam, N-vinylimidazole, N-vinyl-2-methylimidazole, N-vinyl-4-methylimidazole, diallylammonium chloride, vinyl acetate and vinyl propionate,
where the alkyl groups can be substituted with hydroxyl groups, and the monoethylenically unsaturated carboxylic acid C is selected independently of one another for groups e), f), g) from: acrylic acid, methacrylic acid, dimethacrylic acid, ethacrylic acid, maleic acid, citraconic acid, methylenemalonic acid, allylacetic acid, vinylacetic acid, crotonic acid, fumaric acid, mesaconic acid and itaconic acid.

17. The thickened aqueous composition defined in claim 11, which is in the form of a cosmetic product.

18. The thickened aqueous composition defined in claim 11, wherein the cosmetic product is a hair cleanser.

* * * * *